(12) United States Patent
Schönborn et al.

(10) Patent No.: US 7,450,682 B2
(45) Date of Patent: Nov. 11, 2008

(54) METHOD AND DEVICE FOR SPATIAL PRESENTATION OF AN EXAMINATION AREA OF AN OBJECT UNDER EXAMINATION

(75) Inventors: Manfred Schönborn, Gerhardshofen (DE); Frank Grasser, Eggolsheim (DE); Rudolf Heimberger, Würzburg (DE); Herbert Kemeth, Hausen (DE); Winfried Lurz, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/593,403

(22) Filed: Nov. 6, 2006

(65) Prior Publication Data
US 2007/0104309 A1 May 10, 2007

(30) Foreign Application Priority Data
Nov. 7, 2005 (DE) .............. 10 2005 053 022

(51) Int. Cl.
*A61B 6/00* (2006.01)
(52) U.S. Cl. .................................. 378/4
(58) Field of Classification Search ........... 378/4–20, 378/901
See application file for complete search history.

(56) References Cited

U.S. PATENT DOCUMENTS

| | | | | |
|---|---|---|---|---|
| 4,920,491 A * | 4/1990 | Eberhard et al. | ............ | 382/131 |
| 5,053,958 A * | 10/1991 | Tam | ............ | 378/4 |
| 5,073,911 A * | 12/1991 | Ozaki et al. | ............ | 378/17 |
| 5,485,502 A * | 1/1996 | Hinton et al. | ............ | 378/117 |
| 5,602,891 A * | 2/1997 | Pearlman | ............ | 378/62 |
| 5,687,211 A * | 11/1997 | Berger et al. | ............ | 378/196 |
| 5,960,056 A * | 9/1999 | Lai | ............ | 378/4 |
| 6,435,714 B1* | 8/2002 | Bruder | ............ | 378/196 |
| 6,449,337 B1* | 9/2002 | Honda et al. | ............ | 378/117 |
| 6,529,574 B1* | 3/2003 | Hsieh | ............ | 378/4 |
| 6,720,966 B2 | 4/2004 | Barth et al. | | |
| 6,789,940 B2 | 9/2004 | Meyer et al. | | |
| 6,814,490 B1* | 11/2004 | Suhm et al. | ............ | 378/198 |
| 6,928,137 B2* | 8/2005 | Bruder et al. | ............ | 378/4 |
| 7,178,746 B2* | 2/2007 | Gross | ............ | 239/552 |
| 7,187,746 B2* | 3/2007 | Sakaguchi et al. | ............ | 378/8 |
| 7,362,843 B2* | 4/2008 | Basu et al. | ............ | 378/4 |

FOREIGN PATENT DOCUMENTS

| | | |
|---|---|---|
| DE | 199 36 679 A1 | 3/2001 |
| DE | 199 62 666 A1 | 7/2001 |
| DE | 101 40 862 B4 | 4/2003 |
| EP | 1 246 566 B1 | 10/2002 |

* cited by examiner

*Primary Examiner*—Courtney Thomas
*Assistant Examiner*—Alexander H Taningco

(57) ABSTRACT

The invention relates to a method and a device for executing the method for spatial presentation of a predeterminable area under examination. By overlaying a movement of the axis of projection along an axis of examination onto a rotation of an axis of projection around the object under examination, and by interpolating from the recorded projection data sets image data sets for axes of projection not recorded, and by creating a spatial presentation of the area under examination from the projection and image data sets, a method and a device can be provided which increases the speed of an examination for an extended area under examination of an object under examination.

19 Claims, 2 Drawing Sheets

METHOD AND DEVICE FOR SPATIAL PRESENTATION OF AN EXAMINATION AREA OF AN OBJECT UNDER EXAMINATION

CROSS REFERENCE TO RELATED APPLICATIONS

This application claims priority of German application No. 10 2005 053 022.2 filed Nov. 7, 2005, which is incorporated by reference herein in its entirety.

FIELD OF THE INVENTION

The invention relates to a method and to a device for executing the method for spatial presentation of a predeterminable examination area of an object under examination, with a plurality of two-dimensional projection data sets of the area under examination being recorded, with the axis of projection of the x-ray images essentially intersecting a common axis of examination at right angles, with the projection data sets being recorded in each case after a rotation of the axis of projection around the examination axis.

BACKGROUND OF THE INVENTION

Spatial or three-dimensional views of objects to be examined are a major component of diagnostics in medical engineering and are of great importance for the planning and execution of medical interventions. The improved capabilities for analyzing complicated structures within an object to be examined provided by spatial presentation reassure patients and reduce the time spent in planning and undertaking medical interventions. A spatial presentation is of particular advantage for vessel systems to allow a better overview to be obtained. A plurality of different methods for creating a three-dimensional image of an object to be examined is currently known.

Such methods include 3D x-ray systems, especially computer tomography and C-arm systems, magnetic resonance tomography, 3D ultrasound, etc. With currently known x-ray methods which can be employed for interventional treatments it is not possible to examine areas which are larger than the x-ray bundle used for penetrating the object under examination.

Patent application DE 101 40 862 B4 discloses a medical x-ray examination device with a pedestal, with a guide rail mounted on the pedestal, with a first carriage mounted on the guide rail and able to be moved along it, with an x-ray imaging system mounted on the first carriage, and with a patient support device. A second carriage mounted on the guide rail and able to be moved along said rail, on which the patient support device is mounted via an outrigger arm, allows the number of possible x-ray examinations to be increased and makes the system more user-friendly for those operating it.

A method for reconstruction of 3D image data relating to a volume of interest of an object to be examined is known from application DE 199 62 666 A1, in which a plurality of 2D central projections is obtained from different projection directions by means of a flat-panel detector and rays emanating from an a x-ray source. The disadvantage of this method is that only a restricted area can be investigated during an examination, said area being limited by the size of the flat-panel detector. Examination areas which have dimensions larger than the spatial extent of the x-ray bundle used can only be covered by executing an examination a number of times and then going through the tedious process of combining the results.

SUMMARY OF THE INVENTION

The object of the invention is to provide a generic method and also a generic device with which the speed of examination can be increased for an extended area of an object under examination.

The part of the object to be achieved by the method described at the start of this document for spatial presentation of a predeterminable area of an object under examination is achieved by overlaying the rotation of the projection axis onto an offset along the axis of examination, so that image data sets for non-recorded projection axes are interpolated from the recorded projection data, and that a spatial presentation of the area under examination is created from the projection and image data sets.

The axis of projection is usually taken to mean the central ray of the x-ray bundle which an x-ray source emits in a specific direction and which is detected by an x-ray detector, in connection with a specific piercing point of the object under examination. This means that the same projection directions for different piercing points of the central ray are different axes of projection. The axis of examination can for example be viewed as the longitudinal axis of a human body. Alternatively, where no longitudinal axis of a body can be detected, the longitudinal axis of the patient table can be identified as this axis, which is shifted in parallel at the height of the center point of the object to be examined. As a rule the axis of examination always essentially intersects the plane spanned by an x-ray C-arm at right angles.

The area to be examined can exceed the extents of the x-ray bundle during the penetration of the object under examination. The predetermination of the area of the given object to be examined, by the medical personnel for example, allows precisely the relevant subarea of the object under examination to be examined efficiently as regards time. If the examination is started after all the necessary parameters have been set, the method for spatial presentation then generally runs automatically.

The x-ray bundle passing through an examination object has a finite extent which extends for current x-ray systems from a few millimeters, e.g. for computer tomography applications, up to several tens of centimeters, e.g. for C-arm x-ray systems. Because of the extent of the bundle, the latter feature two-dimensional projection data sets, whereas the former can be designated as zero-dimensional data sets.

With the use of x-ray systems for which the dimensions of the x-ray bundle are in the centimeter range, a spatial projection of the x-rayed area can be determined directly from projection data sets recorded from a number of projection directions. With the use of x-ray systems, of which the ray bundle extent lies within the millimeter range only one layer of the object under examination can be reconstructed.

However a three-dimensional presentation can still be realized from reconstructed layers of the area under examination. Only one projection data set is created by means of x-ray imaging for each subsection of the area under examination by means of the inventive method. Image data sets of the same subsection of the area under examination for further projection directions can be interpolated from further, suitable x-ray images. This requires the central rays of adjacent projection data sets with the same projection directions to not be further away from each other than the extent of the x-ray bundle in the direction of movement.

This means that an image data set for these projection directions can be interpolated from adjacent data sets recorded in the same projection directions lying between the adjacent recorded data sets. This interpolated image data set delivers a projection data set for a section of the area under examination, which was only recorded from another direction of projection. Thus interpolated image data sets with different projection directions exist for the same subsection of an area under examination as well as a recorded projection data set with a projection direction with a projection direction which is likewise different from the projection direction of the image data sets.

Any number of projection data sets can be interpolated to image data sets from different projection directions. There are thus sufficient data sets available for a subsection of an area under examination, so that by reconstructing the two-dimensional data sets a three-dimensional image of the area under examination or of the subsection of the area under examination can be created.

It is advantageous in this case that only one x-ray image has to be recorded for each direction of projection and each examination subsection. This means that both the x-ray dose for the patient is reduced and the speed of the examination process is also increased.

In a particular embodiment of the invention a C-arm x-ray imaging system is used to record the two-dimensional projection data sets. This is because it is with precisely these types of device that a large bundle extent of the x-ray bundle passing through the examination object is produced as well as the option of rotating the x-ray imaging system around the object under examination. In particular the inventive method can generally be easily employed with existing C-arm x-ray systems. This allows a low-cost introduction of the inventive method. This especially also enables patient throughput to be increased.

In a further advantageous embodiment of the invention the area under examination is moved along at the axis of examination in order to move the axis of projection along the axis of examination, while a system for recording x-ray images is not moved. This means that the x-ray device itself does not make any translational movements but only one rotational movement, whereas the object under examination is moved continuously or in stages during the examination process along the axis of examination. This can be done for example by moving a patient table on which the object to be examined is positioned. The patient table as a rule has a lower inertia than the system required to record the x-ray images. This means that lower friction and energy consumption can be expected, which reduces operating costs.

In a further advantageous embodiment of the invention, to move the axis of projection along the axis of examination, the x-ray recording system is moved along the axis of examination while the area under examination is not moved. This variation of the method can be required if space restrictions mean that it is impossible to move the patient table but it is possible to move the x-ray recording system. Thus the system for recording x-ray images is guided over the predetermined examination area of the object under examination. This means that the x-ray imaging system makes both a translational and also a rotational movement.

The appropriate guides or robot systems are necessary to implement a translational movement of an x-ray imaging device. In a preferred form patient table and x-ray imaging system can be moved simultaneously against one another along at the axis of examination. This makes sense if neither of the two components, i.e. patient table and x-ray imaging system, has the necessary speed of movement to achieve the speed advantage of the inventive method.

The limit of the relative forwards movement is reached as a rule if, for the backwards and forwards rotation of the rotatable x-ray system, the projection data sets obtained by the movement no longer border on each other for the same directions of projection. For small distances between adjacent, no longer overlapping projection data sets of the same direction of projection, projection data sets can if necessary be interpolated between the no longer overlapping projection data sets. On the one hand this can lead to a reduction of the reliability of the examination results, on the other hand to an acceleration of the examination.

The critical speed of the relative advance is defined by the maximum distance of a defined position of the projection data sets which are now no longer overlaid and the time which the x-ray recording system needs to move from the first reversing point of the rotation to the second reversing point of the rotation and back again, and thereby has a suitable image recording rate of for example 30 images per second. The order of magnitude of the critical speed of the relative advance can be estimated for a Siemens Axiom Artis Dyna CT system currently available on the market at a few centimeters per second.

The speed of critical advance can be increased much more by improved rotational drives, especially orbital drives, with higher speeds of rotation and an x-ray imaging system with suitable image recording rates.

In a preferred embodiment of the invention the rotation is carried between two specified reversing points. This means that the method can be undertaken by means of precisely one x-ray source and precisely one x-ray detector. The x-ray source and the x-ray detector are rotated around the axis of examination and thereby around the object under examination up to a first reversing point, while images, i.e. two-dimensional projection data sets, are being recorded at defined intervals. At the reversing point the x-ray imaging system reverses its direction of rotation and rotates in the opposite direction to a second reversing point. Further projection data sets continue to be recorded during this process.

Alternatively a number of x-ray sources and x-ray detectors which are aligned on different projection directions can be present while a relative movement of the object under examination in relation to the x-ray imaging system is undertaken. With more than precisely one x-ray source and precisely one x-ray detector a choice can be made as to whether a rotation between two reversing points occurs during the examination, or an even or possibly no rotation is required for the x-ray imaging systems.

In a further advantageous embodiment of the invention x-ray images are recorded independently of the direction of rotation. The fact that images of two-dimensional projection data sets are recorded not just in the forwards or the backwards rotation but in both the forwards and backwards rotation of the x-ray imaging system allows the throughput time to be increased by a factor of two with all other conditions remaining the same, or enables the time needed for performing an examination to be reduced by a factor of two.

In a further preferred embodiment of the invention x-ray images are recorded without interrupting the rotation. Associated with this is the requirement for the x-rays to be taken in a period in which the x-ray imaging system is semi-immobile. This means that the rotational movement of the x-ray imaging system within the measurement interval must be negligible, since otherwise artifacts are produced which can falsify the examination results, unless these results are corrected. If it is possible to correct the artifacts the above-mentioned condition does not apply. The recording of x-ray images without reducing the angular speed of the x-ray imaging system also reduces the examination time needed.

In an alternative embodiment of the invention at least one x-ray image is recorded after interruption of the rotation. This can be required for example is an image of an organ is to be recorded in a specific state of movement. However this can also be adopted as a general recording concept if for example the movement of the x-ray imaging system at a specific angular speed in the measurement interval for recording the x-ray image is not negligible.

For example the angular speed of the x-ray imaging system is reduced until it comes to a standstill. The projection data set is then recorded in a specific direction of projection. Subsequently the x-ray imaging system put into motion again to move to the next position in order to record a further projection data set at a specific changed direction of recording there etc. With this recording movement too an expanded recording movement for an examination area of an object under examination is possible.

In a further advantageous embodiment of the invention an interpolation from projection data sets with parallel axes of projection in each case is undertaken. It is especially advantageous for this purpose to use adjacent projection data sets for the same projection directions. Furthermore it is advantageous if projection data sets used for interpolation have a spatial overlapping area for the same projection directions. This enables a two-dimensional image data set for the same projection directions to be determined without any loss of quality and to be related to a recorded projection data set.

The interpolation can be performed for each projection direction for which at least two projection data sets have been recorded. Any number of interpolated projection data sets can be recorded for each projection direction. The accuracy of the examination result in direction of the examination axis can then be increased as required for a defined number of projection directions and in practice depends solely on the computing capacity of the existing data processing device.

In a further preferred execution variant, in the time before the first x-ray image is recorded, a simulation of the rotation of the axis of projection, which is overlaid with a movement of the axis of projection along the axis of examination in accordance with the predetermined examination area, is undertaken. This allows collisions between the x-ray imaging system and/or the support device and thus damage to the x-ray system and also to the equipment of the medical working environment or the personnel to be avoided.

This expediently requires the position of the devices present in the environment to be recorded, which can be done by means of sensors for example. The sensors are connected to the controller which supplies the information about the position of the devices in the area of the simulation. This enables the danger of a collision to be detected at an early stage, without damage being done to the equipment or the x-ray system. If necessary a test run of the x-ray imaging system can be performed before the start of the examination.

In particular a method for spatial presentation of a predeterminable examination area of an object under examination is advantageous, with a plurality of two-dimensional projection data sets of the area under examination being recorded by x-ray images, with the axes of projection of the x-ray imaging system essentially intersecting a common axis of examination at right angles, with the projection data sets being recorded after a rotation of the axis of projection around the axis of examination in each case, with the rotation of the axis of projection being overlaid with a movement of the axis of projection along the axis of examination, with two-dimensional image data sets for axes of projection not recorded being interpolated from the recorded two-dimensional projection data sets such that from adjacent two-dimensional projection data sets essentially adjoining one another in their recording area of parallel axes of projection two-dimensional, preferably seamless image data sets are determined, and that from the two-dimensional projection and two-dimensional image data sets a spatial presentation of the area under examination is created.

The part object to be achieved by the device is achieved by an x-ray system with a support device for an object under examination which can be moved along an axis of examination with an predeterminable area of examination, with an x-ray imaging system movable along the axis of examination, with the x-ray imaging system comprising an x-ray source and an x-ray detector, between which an axis of projection extends centrally in a straight line, with the x-ray imaging system being arranged rotatably around the object under examination, with means for driving the movable support device and/or the movable x-ray imaging system, with a control, by which the drive means and the x-ray imaging system can be controlled such that the movement of the axis of projection can be overlaid with a movement of the axis of projection along the axis of examination, with a data processing unit, with which data sets can be stored and can be processed, as claimed in one of the claims, and with an image display unit for spatial presentation of the area under examination.

In an advantageous embodiment of the invention the x-ray imaging system is embodied as a C-arm x-ray imaging system. A C-arm x-ray imaging system is especially suitable for the method in accordance with the invention, since C-arm x-ray imaging systems are very widely used in clinical environments. This enables the inventive method to be used simply by modifying control instructions and/or by adding the necessary inventive equipment components.

BRIEF DESCRIPTION OF THE DRAWINGS

Further advantages of the inventive method emerge from an exemplary embodiment, which is explained below in greater detail on the basis of the drawing in which.

DETAILED DESCRIPTION OF THE INVENTION

Figure 1:
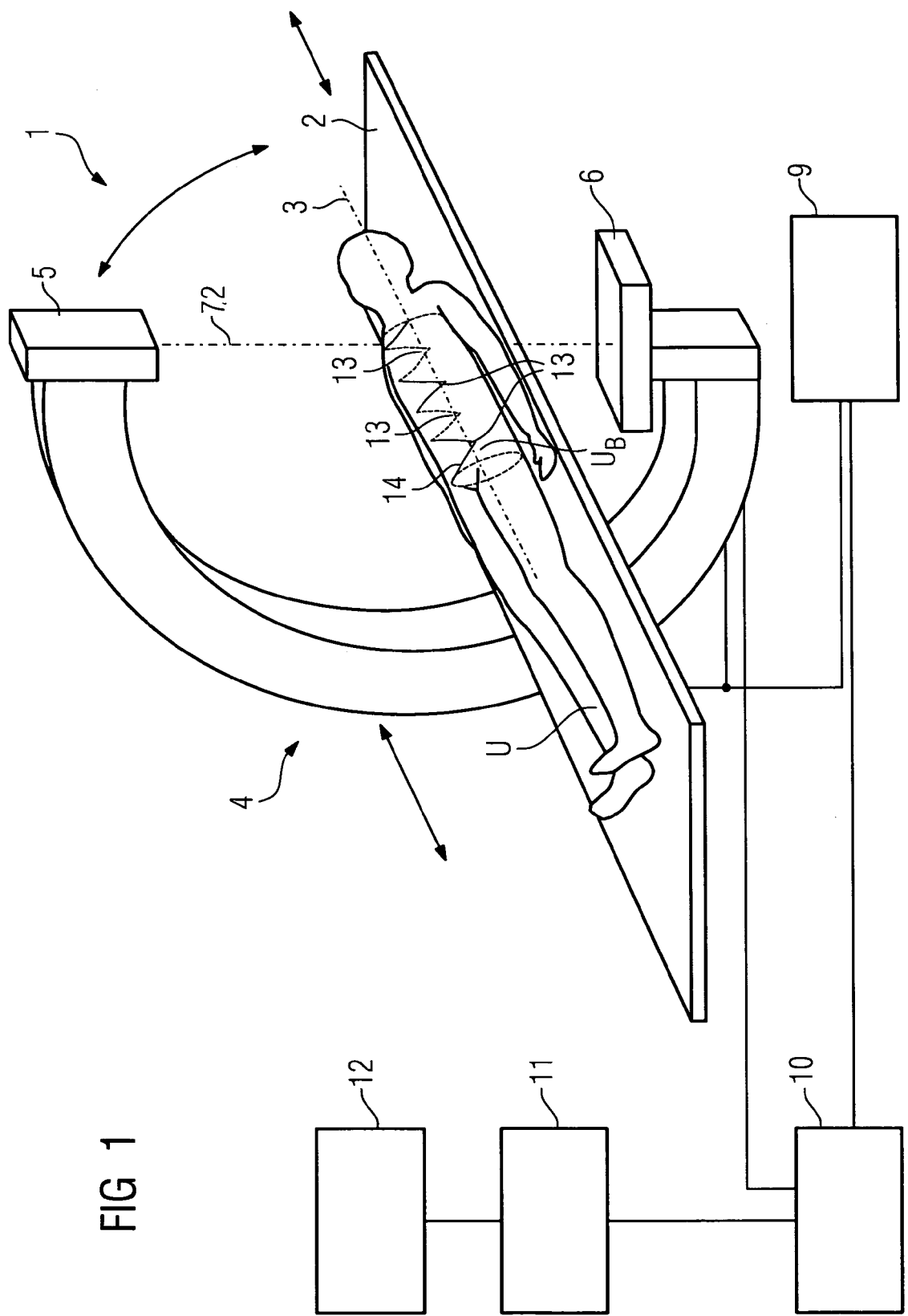
FIG. 1 shows an arrangement for executing of the method in accordance with the invention.

FIG. 1 shows an x-ray system 1, which features a support device 2 for supporting an object under examination U, as a rule the body of a human or of an animal. For the object under examination U, an extended area under examination $U_B$ is to be examined by means of the x-ray system 1. The object under examination U is adapted to the x-ray system 1, positioned on the support device 2 and aligned along an axis of examination 3.

In the exemplary embodiment the axis of examination 3 matches the longitudinal axis of the body of the object under examination U shown. A C-arm type x-ray imaging system 4 is used to record the required data sets. This has an x-ray source 5 and an x-ray detector 6 positioned opposite the x-ray source 5. These are rigidly connected to each other by a C-shaped arm.

The center point of the x-ray source 5 and the center point of the x-ray detector 6 are connected to each other by a virtual axis of projection, which generally coincides with the direction of the central ray of the x-ray bundle emitted by the x-ray source 5. The axis of projection changes its location and its direction during the course of the examination and in FIG. 1 coincides with an axis of projection 72. The x-ray imaging system 4 is support to allow movement along the axis of examination 3. The support device 2 can also be moved along the axis of examination 3. Furthermore the C-arm 4 is supported so as to enable it to be rotated around the object under examination U.

Both the longitudinal movement of the C-arm 4 and of the support device 2 as well as the rotation of the C-arm 4 around the object under examination U are driven by means a drive element 9. The drive element 9 is connected to a controller 10 which controls the forwards movement of the C-arm 4 or of the support device 2, the speed of rotation of the C-arm 4 around the object under examination U as well as the image recording of the C-arm 4.

Two-dimensional projection data sets are recorded by means of the x-ray imaging system 4 while this system is being rotated around the object under examination U and moved in relation to the object under examination U. In this case the x-ray imaging system 4 uses the highest possible image recording rate of for example 30 images per second. For the starting point of the examination the C-arm 4 is positioned so that the x-ray bundle still sufficiently passes through the start of the area under examination $U_B$, with the axis of projection being freely selectable in the start position.

After the start the support device 2 is accelerated at a constant speed of movement of one centimeter per second in the direction opposite to the position of the area under examination $U_B$. Simultaneously the C-arm 4 begins with the image recording and the rotation around the object under examination U. Within the area under examination $U_B$ of the object under examination U the course of the totality of the intersection points 14 of the axes of projection with the surface of the object under examination U is illustrated schematically.

The overlaying of the movement of the object under examination U against the x-ray imaging system 4 along the axis of examination 3 in connection with the rotation of the x-ray recording system 4 around the object under examination U produces the course of the intersection points 14 of the totality of the axes of projection with the surface of the object under examination U shown. The rotation of the x-ray system 4 features reversing points 13. There are two reversing points 13, namely, a reversing point 13 on the left and the right looking along the axis of examination 3 of the x-ray imaging system 4. The course of the intersection points 14 of the totality of the axes of projection with the surface of the object under examination can advantageously be changed by changing the direction of movement of the object under examination U against the x-ray imaging system 4 and changing the direction of rotation of the x-ray imaging system 4—at the discretion of the specialist personnel.

During the recording movement a plurality of projection data sets is recorded which is forwarded to a data processing unit 11. The examination lasts until the end of the area under examination $U_B$ is reached. The projection data sets are stored in the data processing unit 11 and, where possible, processed as the examination is underway.

The data processing unit 11 executes an interpolation of the same projection directions for adjacent projection data sets. Image data sets are determined between the two projection data sets used in each case for the same projection directions which have a predeterminable increment.

The increment describes the spatial displacement between two image data sets of the same projection direction adjacent in their recording area. The increment of the image data sets determined between the two adjacent projection data sets of the same projection direction corresponds expediently in this case to the distance along the axis of examination 3 between two projection data sets immediately following one other in different directions of projection. This allows the increment of the interpolated image data sets to be reconciled with the increment of the projection data sets. A plurality of interpolated image data sets is now determined for two adjacent projection data sets of the same projection direction in each case.

Image data sets can be interpolated for all directions of projection for which at least two adjacent projection data sets of the same direction of projection are available which border on each other in the recording area.

A reconstruction for spatial presentation of the entire examination area $U_B$, which is output on the display unit 12 and is available to a medical personnel in the data processing unit 11, is also calculated from the image data sets determined in conjunction with the recorded projection data sets. This allows a larger examination area $U_B$ of the object under examination U to be examined.

Figure 2:
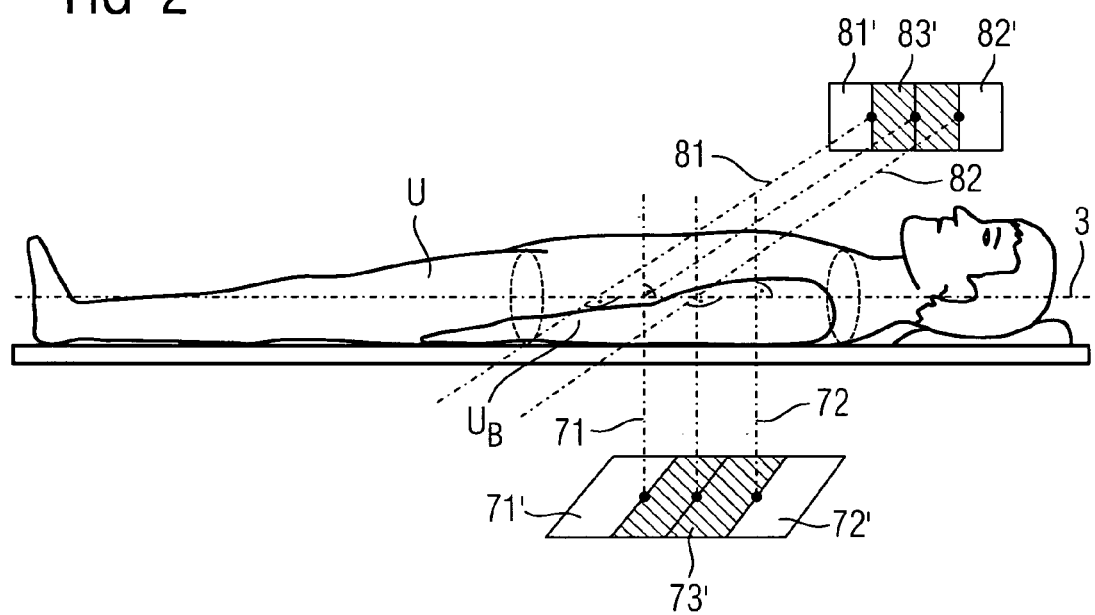
FIG. 2 shows a diagram for creating interpolated image data sets as schematic illustrations.

FIG. 2 shows an object under examination U which features an area under examination $U_B$ and extends along an examination axis 3. Four axes of protection are shown for example in the area under examination $U_B$ which are paired in the same direction and for which one direction of a pair is orthogonal to the direction of the other pair in each case as well as to the direction of the axis of examination 3.

The axes of projection represent the direction of recording of the projection data sets and their recording position on the object under examination U. Thus the number of the axes of projection occurring in an examination depends on the relative speed of movement of the object under examination U in relation to the x-ray imaging system 4 from FIG. 1, the image recording rate of the x-ray imaging system 4 from FIG. 1 and also the position of the reversing points 13 from FIG. 1 of the x-ray imaging system 4 from FIG. 1 etc.

FIG. 2 shows a first pair of projection axes 71 or 72 to which two-dimensional projection data sets 71' and 72' are assigned. The projection data sets 71' or 72' are adjacent and have the same directions of projection.

Furthermore the projection data sets 71' or 72' directly border on one another in their recording area. Shown in the Figure rotated at 90 degrees around the axis of examination 3 and moved along the axis of examination 3 is a second pair of projection axes 81 or 82 to which the projection data sets 81' and 82' are assigned. These projection data sets 81' or 82' also border on each other and have the same projection directions but differ from the first pair of projection data sets 71' or 72' in that their projection direction is rotated by 90 degrees to the projection directions of the first pair 71' or 72'.

Furthermore the piercing point of the axis of examination 3 is different for each projection axis 71 or 72 or 81 or 82 different, which is caused by the movement of the object under examination U in relation to the x-ray recording system 4 from FIG. 1.

The projection data sets 71' or 72' or 81' or 82' represent images of the area under examination $U_B$. Since these directly border one another, the method can be ideally exploited.

As can be seen from FIG. 2, any number of image data sets 73' with different proportions of the projection data sets 71' and 72' can be interpolated from the projection data sets 71' or 72'. Likewise any number of image data sets 83' with different proportions of the projection data sets 81' and 82' can be determined from the projection data sets 81' or 82'.

If projection data sets do not border on each other but overlap in their recording area, redundant information is produced in the projection data sets 71' or 72' or 81' or 82', which reduces the speed of the method. If the recording areas of adjacent projection data sets 71' or 72' or 81' or 82' are spaced from each other so that they neither overlap nor directly adjoin one another, the quality of the examination result since information about the object under examination is not recorded.

FIG. 2 shows that with the aid of the interpolation of two adjacent which border one another in their recording area 71' or 72' and 81' or 82' if the same direction image data sets can be created which no longer differ from a projection data set in the point of intersection of the axis of examination 3 but only by being rotated at 90 degrees.

This is the case for example for projection data set 82' and 73' as well as for 71' and 83'. A complete set of two-dimensional data sets can be created from these relevant projection and image data sets for a relevant subsection of the area under examination $U_B$, to make possible a reconstruction of a spatial presentation of the area under examination.

FIG. 2 shows image data sets 73' or 83' which are each made up of about 50 percent of the associated respective projection data sets 71' or 72' or 81' or 82'. However the composition of the image data set 73' is for example freely selectable, for example 10 percent of projection data set 71' and 90 percent of projection data set 72'.

The composition of the image data set 73' or 83' is however directly connected to the above-mentioned increment. By changing the percentage share of the relevant projection data set 71' or 72' or 81' or 82' the increment of the interpolated image data set 73' or 83' can be varied along the axis of examination 3 and the increment of the interpolated image data sets 73' or 83' can be adapted to the increment of the recorded projection data sets 71' or 72' or 81' or 82'.

The invention claimed is:

1. A method for spatially presenting an x-ray image of an area under examination of an object, comprising
   recording a plurality of two-dimensional projection data sets of the area under examination by an x-ray imaging system, wherein each of the projection data sets is recorded along an axis of projection of the x-ray imaging system intersecting an axis of examination at a right angle;
   simultaneously rotating the axis of projection around the axis of examination and moving the axis of projection along the axis of examination while recording the projection data sets;
   interpolating an image data set for an angle of projection not recorded from the projection data sets; and
   combining the projection data sets and the image data set resulting from said interpolating to produce a combined data set; and
   processing the combined data set to create an x-ray image of the area under examination, wherein an increment of the imaged area under examination results from the combining of the projection data sets and the interpolated image data set.

2. The method as claimed in claim 1, wherein the x-ray imaging system is a C-arm x-ray imaging system.

3. The method as claimed in claim 1, wherein the movement of the axis of projection along the axis of examination is achieved by moving the area under examination along the axis of examination while the x-ray imaging system is not moved.

4. The method as claimed in claim 1, wherein the movement of the axis of projection along the axis of examination is achieved by moving the x-ray imaging system along the axis of examination while the area under examination is not moved.

5. The method as claimed in claim 1, wherein the axis of projection is rotated between two predeterminable reversing points.

6. The method as claimed in claim 1, wherein the projection data sets are recorded independently of a direction of the rotation.

7. The method as claimed in claim 1, wherein the projection data sets are recorded without an interruption of the rotation.

8. The method as claimed in claim 1, wherein at least one of the projection data sets is recorded after an interruption of the rotation.

9. The method as claimed in claim 1, wherein the image data set is interpolated from the projection data sets having parallel axes of projection.

10. The method as claimed in claim 1, wherein the simultaneous rotation of the axis of projection around the axis of examination and the movement of the axis of projection along the axis of examination is simulated before the recording.

11. The method as claimed in claim 1, wherein the axis of projection of the x-ray imaging system is a central ray of an x-ray bundle emitted by the x-ray imaging system.

12. The method as claimed in claim 1, wherein the axis of examination is a longitudinal axis of the object or a longitudinal axis of a table supporting the object.

13. A medical x-ray system for presenting a spatial x-ray image of an area under examination of an object, comprising:
   a support device that supports the object;
   an x-ray imaging system that records a plurality of two-dimensional projection data sets of the area under examination, wherein each of the projection data sets is recorded along an axis of projection of the x-ray imaging system intersecting an axis of examination at a right angle;
   a drive device that drives the support device and the x-ray imaging system;
   a controller connected to the drive device that controls a simultaneous movement of the axis of projection along the axis of examination and a rotation of the axis of projection around the axis of examination;
   a data processing unit connected to the controller that:
      interpolates an image data set for an angle of projection not recorded from the projection data sets,
      combines the projection data sets and the image data set resulting from the interpolation to produce a combined data set;
      processes the combined data set to create spatial x-ray image of the area under examination, wherein an increment of the imaged area under examination results from the combination of the projection data sets and the interpolated image data set,
      stores the projection data sets, the image data set, and the spatial x-ray image; and
   an image display unit that displays the spatial x-ray image of the area under examination.

14. The x-ray system as claimed in claim 13, wherein the x-ray imaging system is a C-arm x-ray imaging system.

15. The x-ray system as claimed in claim 13, wherein the drive device moves the support device along the axis of examination while the x-ray imaging system is not moved.

16. The x-ray system as claimed in claim 13, wherein the drive device moves the x-ray imaging system along the axis of examination while the support device is not moved.

17. The x-ray system as claimed in claim 13, wherein the axis of projection of the x-ray imaging system is a central ray of an x-ray bundle emitted by the x-ray imaging system.

18. The x-ray system as claimed in claim 13, wherein the axis of examination is a longitudinal axis of the object or a longitudinal axis of the support device.

19. The x-ray system as claimed in claim 13, wherein the image data set is interpolated from the projection data sets having parallel axes of projection.

* * * * *